(12) United States Patent
Sterrett et al.

(10) Patent No.: US 8,298,247 B2
(45) Date of Patent: Oct. 30, 2012

(54) SUTURE TENSIONING DEVICE

(75) Inventors: Jerry Sterrett, Naples, FL (US);
Ricardo Albertorio, Naples, FL (US);
Jacob Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 963 days.

(21) Appl. No.: 12/149,510

(22) Filed: May 2, 2008

(65) Prior Publication Data
US 2008/0275477 A1 Nov. 6, 2008

Related U.S. Application Data

(60) Provisional application No. 60/915,612, filed on May 2, 2007.

(51) Int. Cl.
*A61B 17/04* (2006.01)
(52) U.S. Cl. .......... 606/144; 606/103; 606/148
(58) Field of Classification Search .......... 606/103, 606/74, 139, 144–146, 148; 623/13.13
See application file for complete search history.

(56) References Cited

U.S. PATENT DOCUMENTS

| | | | |
|---|---|---|---|
| 3,959,960 A | 6/1976 | Santos | |
| 5,143,082 A * | 9/1992 | Kindberg et al. | 600/562 |
| 5,522,827 A | 6/1996 | Combs et al. | |
| 5,578,057 A | 11/1996 | Wenstrom, Jr. | |
| 5,944,739 A | 8/1999 | Zlock et al. | |
| 7,666,196 B1 * | 2/2010 | Miles | 606/144 |
| 2003/0208210 A1 * | 11/2003 | Dreyfuss et al. | 606/144 |
| 2004/0267318 A1 * | 12/2004 | Boucher et al. | 606/232 |
| 2005/0240226 A1 * | 10/2005 | Foerster et al. | 606/232 |
| 2006/0271060 A1 * | 11/2006 | Gordon | 606/103 |
| 2006/0276804 A1 * | 12/2006 | Molz et al. | 606/103 |

FOREIGN PATENT DOCUMENTS

| | | |
|---|---|---|
| WO | WO 03/049620 | 6/2003 |
| WO | WO 2006/128092 | 11/2006 |

* cited by examiner

*Primary Examiner* — Ellen C Hammond
(74) *Attorney, Agent, or Firm* — Dickstein Shapiro LLP

(57) ABSTRACT

A device for tensioning suture which includes a cannulated tube that allows a suture to be fed through at least a portion of the tube. An adjustment device (for example, a wheel or a knob) is actuated to turn a threaded post on the end of the tube. A length of suture passes through at least a portion of the cannulated tube and is secured into a forked pin attached to the adjustment device. Turning the adjustment device draws against the suture, increasing therefore the tension on the suture. The suture tensioning device may be employed in conjunction with a tensiometer.

8 Claims, 19 Drawing Sheets

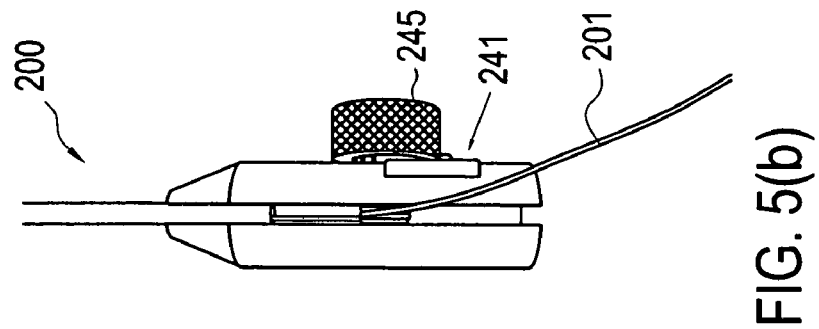
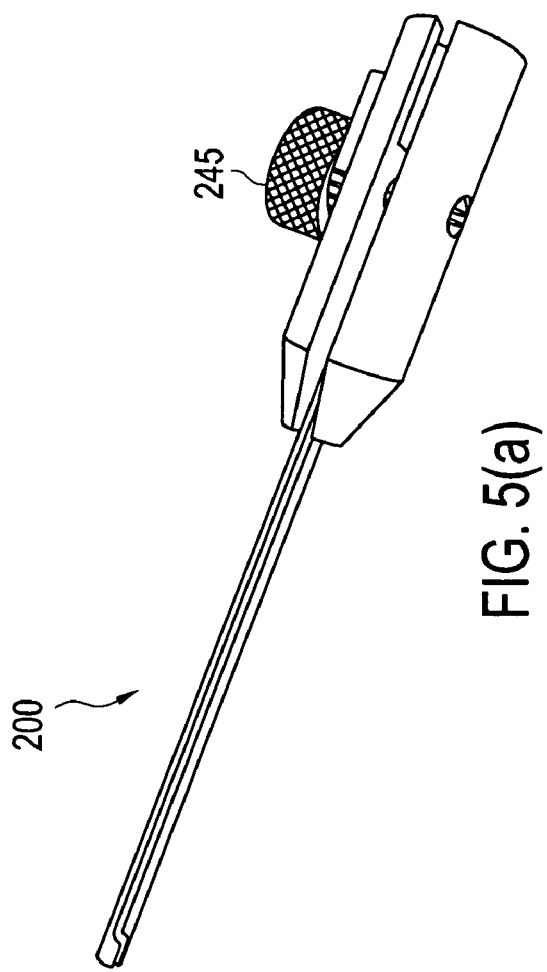
FIG. 5(b)
FIG. 5(a)

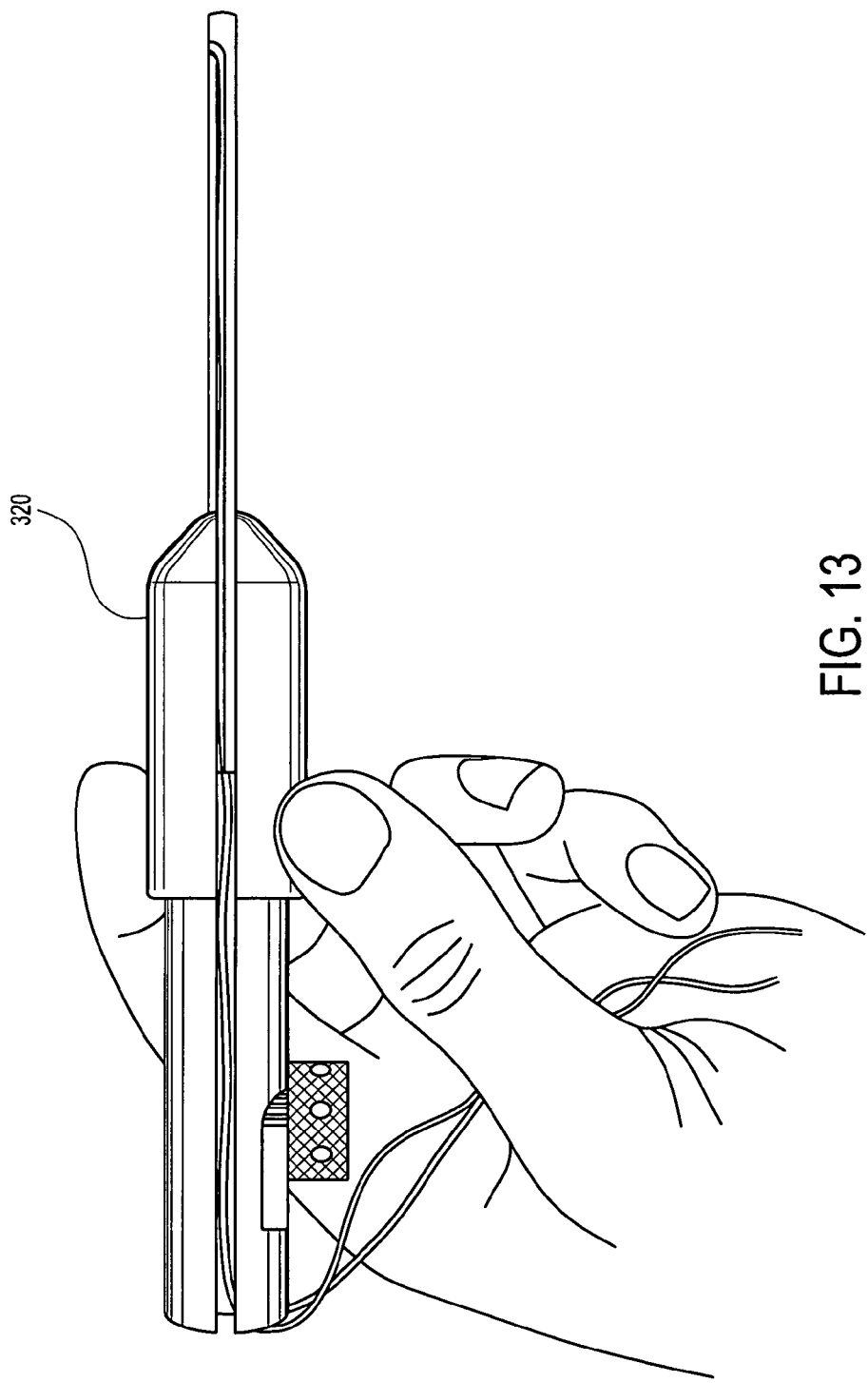

SUTURE TENSIONING DEVICE

CROSS-REFERENCE TO RELATED APPLICATIONS

This application claims the benefit of U.S. Provisional Application Ser. No. 60/915,612, filed May 2, 2007, the entire disclosure of which is incorporated by reference herein.

FIELD OF THE INVENTION

The present invention relates to methods and instruments for tensioning of sutures and, more specifically, to a novel suture tensioning device.

BACKGROUND OF THE INVENTION

Bone fixation using cerclage wire is a surgical procedure for securing fractured or weakened bone. Procedures in which bone cerclage may be indicated include, for example, humeral stem fracture repair and total shoulder surgery. After the cerclage wires are tensioned and wrapped, excess wire is cut off. The wire ends are tucked down to be out of the way. Wire ends that are tucked down improperly, or that become loose, can cause irritation and damage and may require additional revision.

An improved surgical technique for attaching two sections of tissue, or for encircling a bone, with a high strength suture material is needed. Instruments and methods for repairing a bone fracture or for attaching two sections of tissues where placement of a suture, wire or cable is conducted without the tissue damage and irritation presented using cerclage wires are also needed.

SUMMARY OF THE INVENTION

The instruments and methods of the present invention provide apparatus and methods for tensioning suture attached to tissue (for example, graft or bone segments).

The present invention provides a suture tensioning device used for applying tension to a length of suture (for example, high strength suture). The suture tensioning device includes a cannulated tube that allows a suture to be fed through at least a portion of the tube. An adjustment device (for example, a wheel or a knob) is actuated to turn a threaded post on the end of the tube. A length of suture passes through at least a portion of the cannulated tube and is secured into a forked pin attached to the adjustment device. Turning the adjustment device draws against the suture, increasing therefore the tension on the suture. The suture tensioning device may be employed in conjunction with a tensiometer.

The invention also provides a method of tissue fixation (for example, graft or bone fixation) including wrapping the tissue (for example, a graft or fractured bone) with a length of high strength suture material and forming a slip knot in the length of suture. A post leg of the length of suture is threaded through at least a portion of the cannulated tube of the suture tensioning device and is secured into a forked pin attached to the adjustment device. Turning the adjustment device (for example, a wheel or a knob) pulls the suture taut and exerts tension on the suture. A scale may be provided on the suture tensioning device to indicate the relative amount of tension being applied. The tension to be applied by the surgeon on the suture depends on the tissue characteristics (for example, the bone quality) and other factors.

Other features and advantages of the invention will become apparent from the following description of the invention, which refers to the accompanying drawings.

BRIEF DESCRIPTION OF THE DRAWINGS

FIGS. 5(a) and 5(b) illustrate perspective views of a suture tensioning device according to a second embodiment of the present invention.

FIG. 13 illustrates the suture tensioning device of FIG. 6 with suture threaded thereon.

DETAILED DESCRIPTION OF THE PREFERRED EMBODIMENTS

Figure 1:
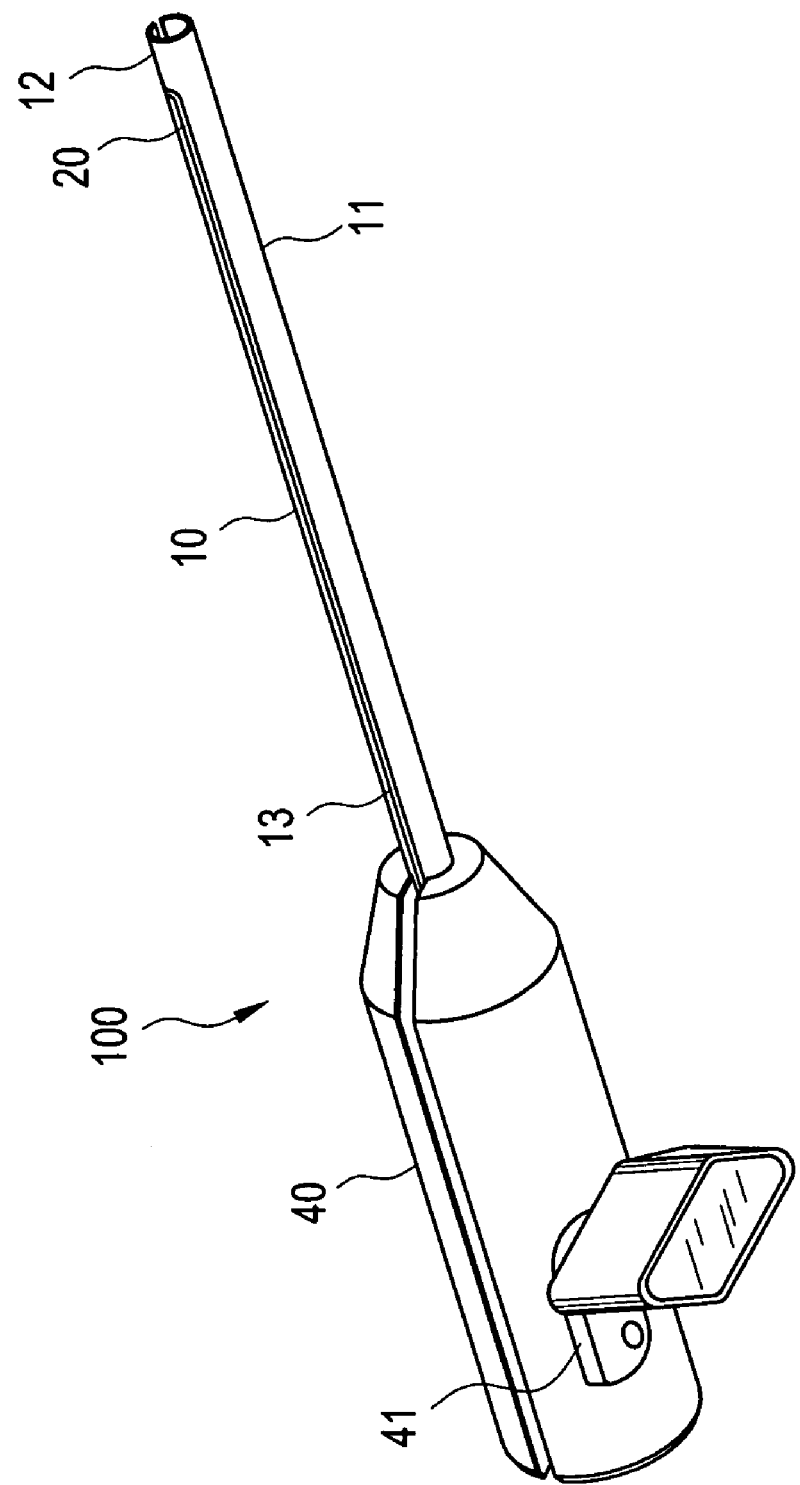
FIG. 1 illustrates a perspective view of a suture tensioning device according to a first embodiment of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a suture tensioning device used for applying tension to a length of suture (for example, high strength suture). The suture tensioning device includes a cannulated tube provided with an opening (for example, a longitudinal slit, or an opening at the distal end of the tube) that allows a suture to be fed through at least a portion of the tube. An adjustment device (for example, a wheel or a knob) is rotated to turn a threaded post on the end of the tube. A length of suture passes through the opening (for example, the longitudinal slit) of the cannulated tube and is secured into a forked pin attached to the adjustment device. Turning the adjustment device draws against the suture, increasing therefore the tension on the suture. The suture tensioning device may be employed in conjunction with a tensiometer.

The invention also provides a method of tissue fixation (for example, graft of bone fixation) including wrapping the tissue (for example, a graft or fractured bone) with a length of high strength suture material and forming a slip knot in the length of suture. A post leg of the length of suture is threaded through at least a portion of the cannulated tube of the suture tensioning device and is secured into a forked pin attached to the adjustment device. Turning the adjustment device (for example, a wheel or a knob) pulls the suture taut and exerts tension on the suture. A scale may be provided on the suture tensioning device to indicate the relative amount of tension being applied. The tension to be applied by the surgeon on the suture depends on the tissue characteristics (for example, the bone quality) and other factors.

Referring now to the drawings, where like elements are designated by like reference numerals, FIGS. 1-6 illustrate various components of a suture tensioning device 100, 200, 300 of the present invention.

Tensioning device 100 includes a cannulated elongated body 10 having a distal end 12 and a proximal end 13, as shown in FIGS. 1-4. The body 10 of the suture tensioning device 100 includes a cannulated shaft or tube section 11. As more clearly shown in FIG. 2, cannulated shaft 11 is provided with a longitudinal slit 20 having a specific configuration and dimensions that allow a suture strand to freely pass through cannulated shaft.

Figure 2:
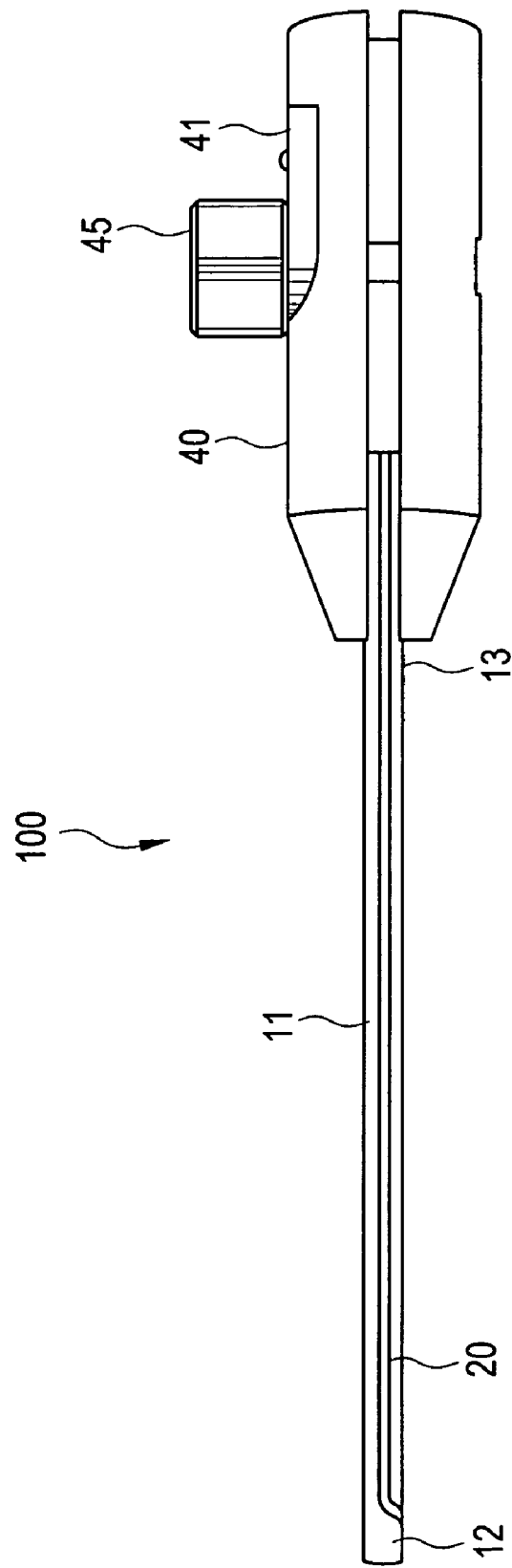
FIG. 2 is a side view of the suture tensioning device of the present invention.
Figure 3A:
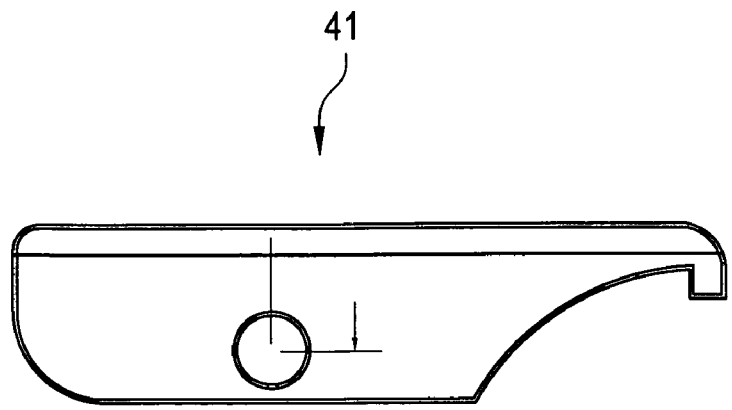
FIGS. 3(a)-(b) illustrate various views of the lever of the suture tensioning device of the present invention.
Figure 3B:
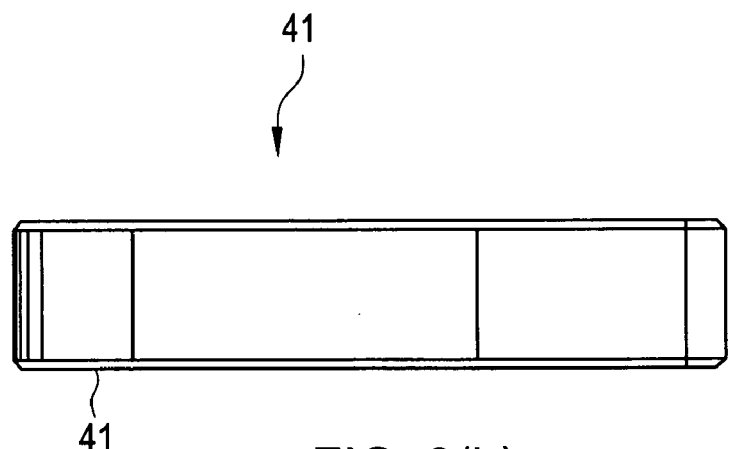
Figure 4:
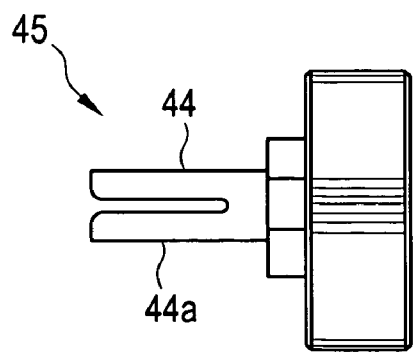
FIG. 4 illustrates various views of the adjustment device provided with a forked pin of the suture tensioning device of the present invention.

Cannulated elongated body 10 is provided at its proximal end 13 with a handle 40, as shown in FIGS. 1-5. Lever 41 (FIGS. 3(a)-(b)) and adjustment device or wheel 45 are assembled on the handle 40, as illustrated in FIGS. 1-2. Adjustment device (wheel) 45 is provided with a forked pin 44, 44a that allows a suture strand passed through the slit 20 to be secured in the tins of the forked pin 44, 44a. Adjustment wheel 45 is designed to allow a user to easily maneuver and turn the wheel during a suture tensioning procedure. Adjustment wheel 45 is also designed to be released from the device 100 by either actuating lever 41 (for example, by pushing lever 41) or by pulling the wheel out of the device.

In use, a length of suture (for example, a graft passing suture which exits percutaneously after the graft is pulled into a femoral or tibial socket) passes through the longitudinal slit 20 of the cannulated tube 11 and is secured into the forked pin 44, 44a attached to the adjustment wheel 45. To secure the suture in the forked pin 44, 44a of adjustment wheel 45, the wheel is removed, and the suture is fed through the instrument. The wheel can be released for removal by actuating the wheel in a first direction (for example, by either pushing the lever 41 or by pulling the wheel out completely). The adjustment wheel 45 is then reinserted into the instrument so that the suture is captured in the forked pin 44, 44a. Reinsertion of the wheel is conducted by actuating the wheel in a second direction (which may be different from the first direction), for example, by pushing the wheel into the handle. Turning the adjustment wheel 45 counterclockwise draws against the suture, increasing therefore the tension on the suture. The suture tensioning device 100 may be employed in conjunction with a tensiometer.

FIGS. 5(a) and 5(b) illustrate another embodiment of a suture tensioning device 200 of the present invention. Suture tensioning device 200 is similar to suture tensioning device 100 described in detail above, except that the configuration of the adjustment device is different (i.e., wheel 45 of device 100 is replaced by a knob 245 of device 200). Knob 245 of device 200 is configured to be removed from the device, to allow passage of at least one suture strand through the slit, and to be subsequently reinserted over the fed suture strand.

In use, knob 245 is first removed from the suture tensioning device 200 by actuating the knob in a first direction. Subsequently, a length of suture 201 (for example, a graft passing suture which exits percutaneously after the graft is pulled into a femoral or tibial socket) is fed through the device so that the suture passes through the longitudinal slit of the cannulated tube and is secured into a forked pin attached to the knob 245. The knob 245 is then reinserted over the fed suture 201 by actuating the knob in a second direction, which may be different from the first direction. The knob can be released by either pushing the lever or by pulling the knob out of the device. Turning the knob counterclockwise draws against the suture, increasing therefore the tension on the suture. The suture tensioning device 200 may be employed in conjunction with a tensiometer.

Figure 6:
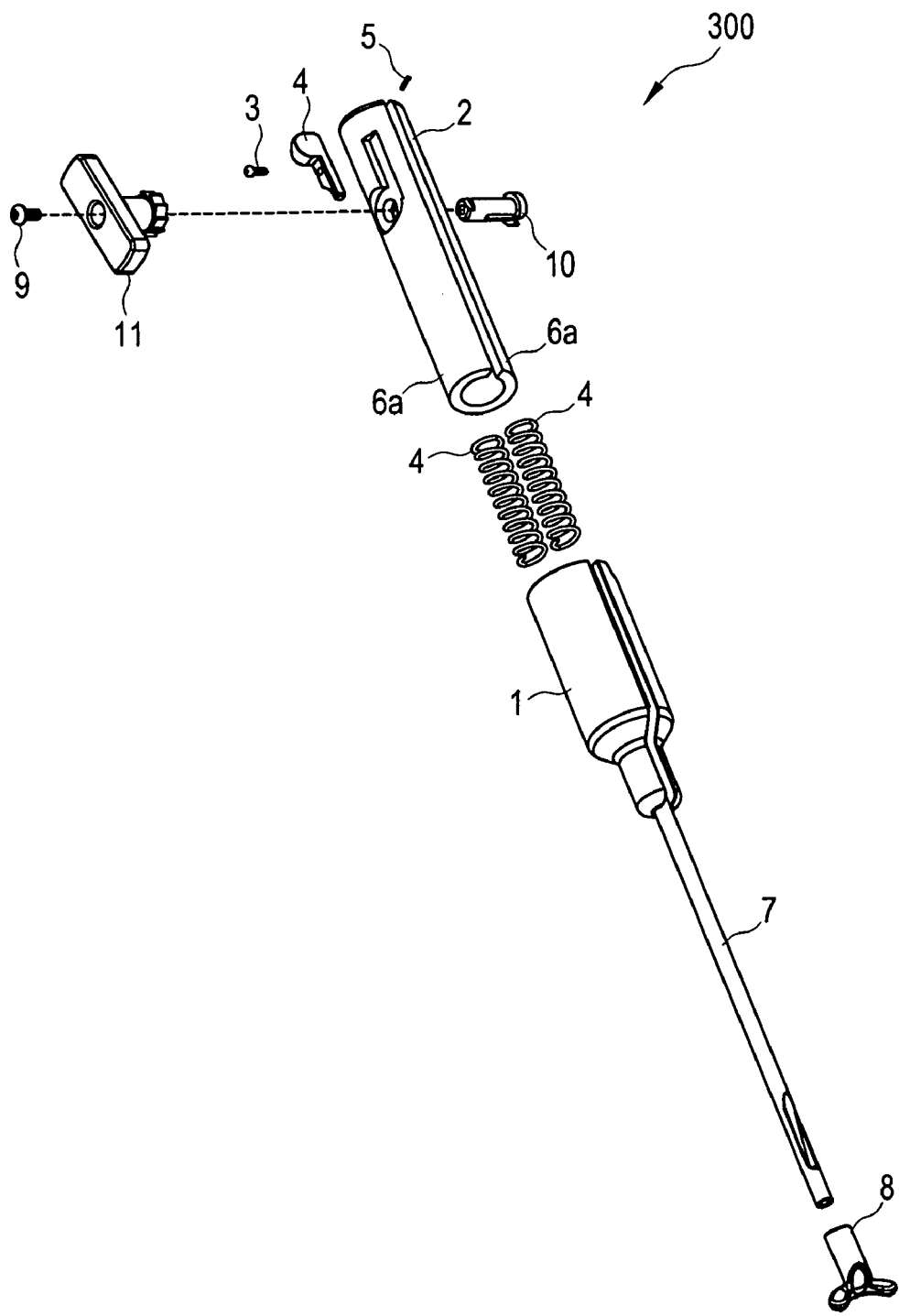
FIG. 6 illustrates an expanded view of a suture tensioning device according to a third embodiment of the present invention.

FIG. 6 illustrates a third embodiment of a suture tensioning device 300 of the present invention. Suture tensioning device 300 is similar to suture tensioning device 200 described in detail above, except that the configuration of the shaft 11 and the longitudinal slit 20 is different (i.e., slit 20 of device 200 is replaced by a distal opening in the shaft of the device 300) and that the device 300 is provided with a built-in tensiometer (for example, a plurality of built-in compression springs) to gage graft tension. As in the previously-described embodiments, the device permits tensioning of the graft-passing suture percutaneously and holds the tension while the graft is fixed from inside the joint with fixation devices (for example, interference screws). The device and method of suture tensioning of this embodiment is useful in double bundle repairs and, particularly, in shoulder applications where the device is used as a knot pusher/suture tensioner combo.

As illustrated in FIG. 6, tensioning device 300 includes outer handle sleeve 1, handle slide 2, pin (for example, spiral pin) 3, ratchet lever 4, ratchet lever spring 5, at least one compression spring 6 (for example, two compression springs 6 as shown in FIG. 10), and shaft 7. A tensiometer foot 8 may be provided at the most distal end of shaft 7. Ratchet knob 311 is attached to handle slide 2 by screw 9 (for example, a panhead Phillip screw 9) and by ratchet shaft 310.

The present invention may be used to secure any type of tissue, for example bone, cartilage, ligament, graft or tendon, such as a biceps tendon or a rotator cuff, which require suture attachment and appropriate tension. An exemplary method of suture tensioning technique employed in a bone fracture repair, for example, may comprise the steps of: (i) providing at least two bone segments undergoing a stem fracture repair and suture tensioning procedure; (ii) providing a fixation device (for example, a bone screw or plug) in the vicinity of the bone segments; (iii) wrapping a length of suture (for example, a high strength suture) attached to the fixation device around the bone segments; (iv) threading the suture strand through the tensioning device 100, 200, 300 described above; and (v) turning the adjustment device to exert tension on the suture.

An exemplary method of suture tensioning technique employed in a graft fixation and tensioning procedure may comprise the steps of: (i) providing graft passing sutures to a graft undergoing graft fixation and tensioning; (ii) pulling the graft with the passing sutures into a tunnel or socket (for example, a femoral or tibial socket); (iii) threading at least one of the passing sutures through the tensioning device 100, 200, 300 described above; and (iv) turning the adjustment device to exert a desired tension on the passing suture. The graft may be fixed or fixated within the joint (i.e., within the tunnel or socket) with fixation devices known in the art (for example, screws) and by known methods in the art.

An exemplary method of all inside button fixation for ACL reconstruction using a suture tensioning device 100, 200, 300 of the present invention is illustrated with reference to FIGS. 7-15(b).

Figure 7:
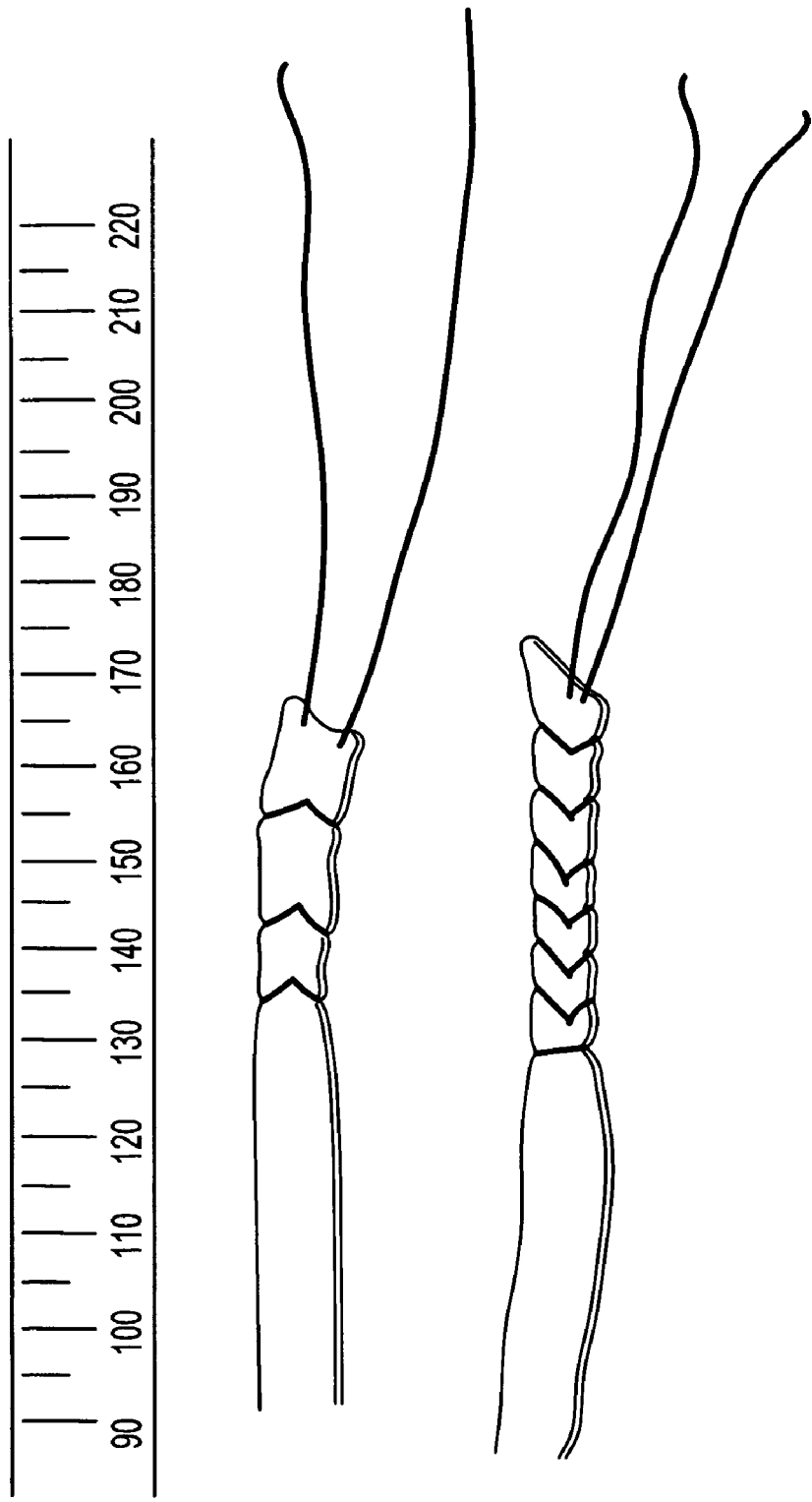
FIGS. 7-12(b) illustrate subsequent steps of an exemplary all inside button fixation for ACL reconstruction using a suture tensioning device of the present invention.
Figure 8:
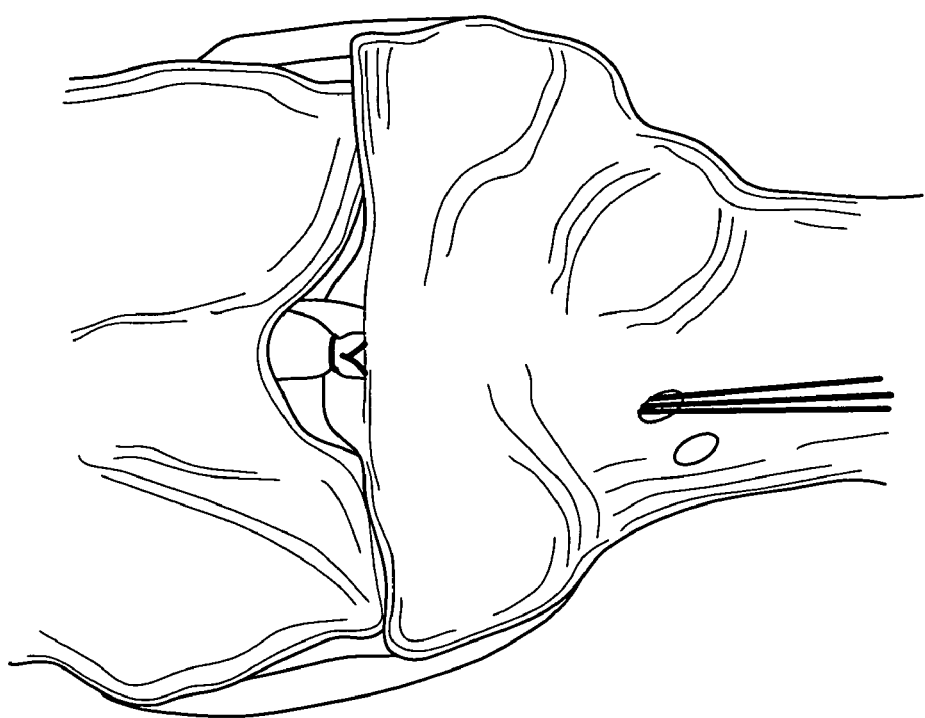
Figure 9:
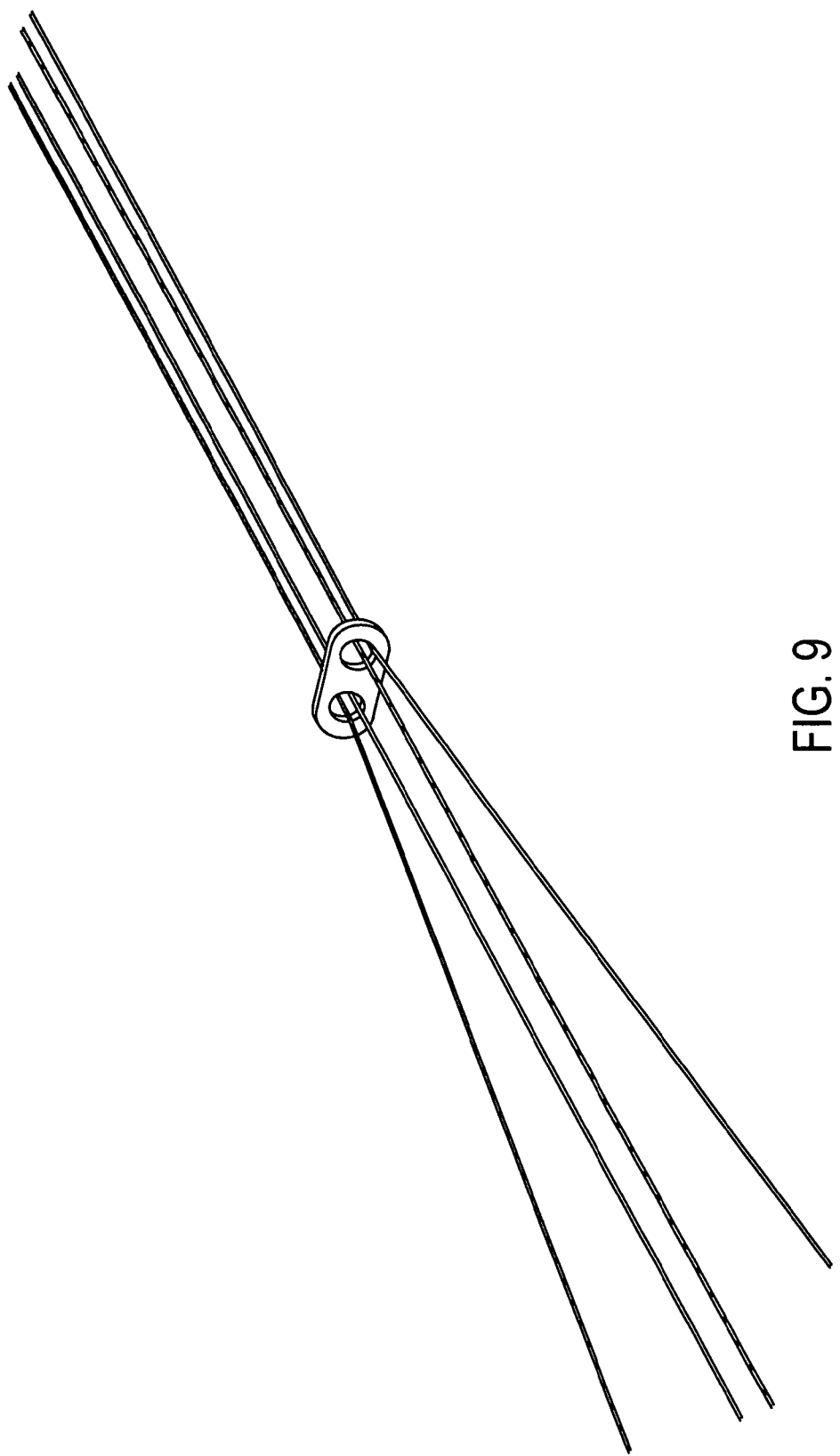

As shown in FIG. 7, one end of graft is whip stitched with suture (for example, Fiberloop with a first color) while the other end of the graft is whip stitched with suture (for example, Tigerloop with a second color). With reference to FIGS. 8 and 9, the graft is passed into femur (with an Arthrex Retrobutton™, for example) and the tibial end of the graft is passed into the tibial socket. Whip stitch sutures will exit about 3 mm hole through cortex. One suture from each end of the graft is passed through a button (for example, a two-hole button or a four-hole button). For example, FIG. 9 illustrates sutures passed through a two-hole button.

Figure 10A:
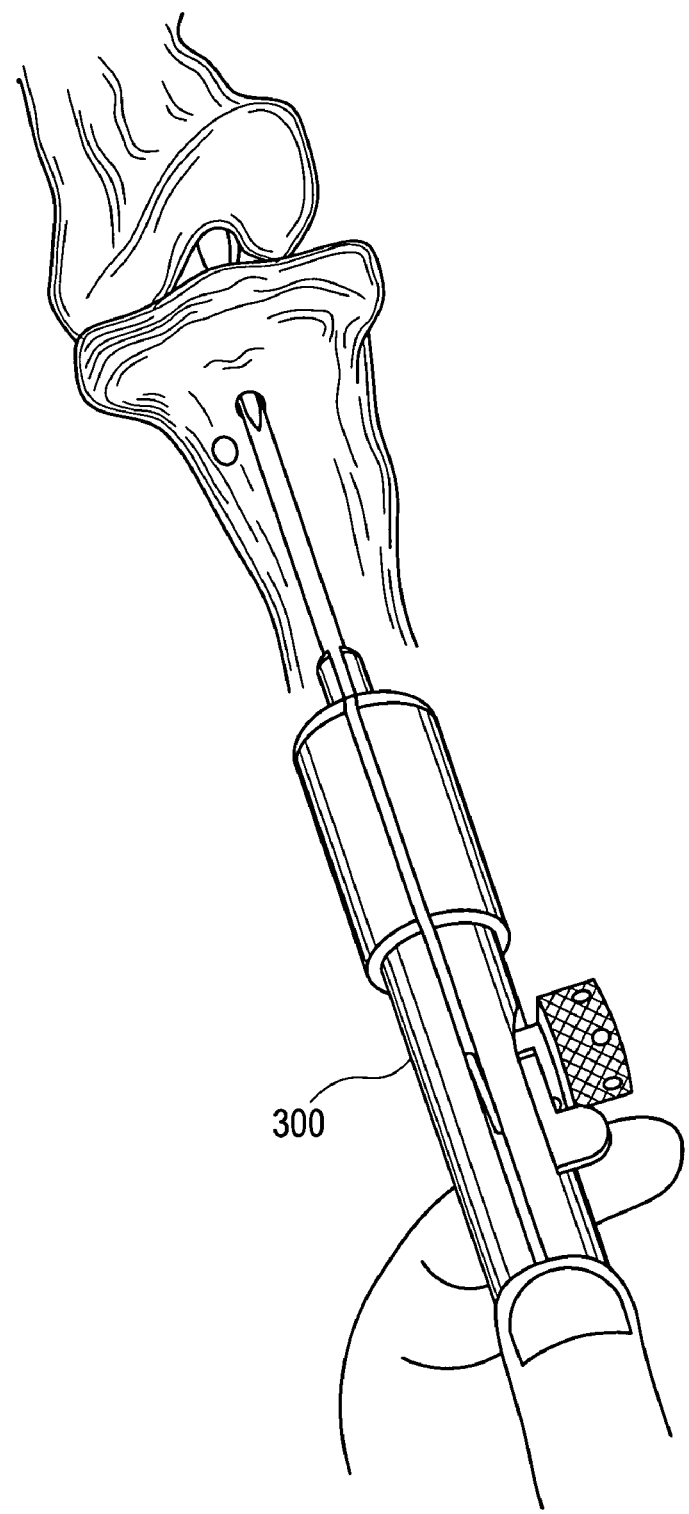
Figure 10B:
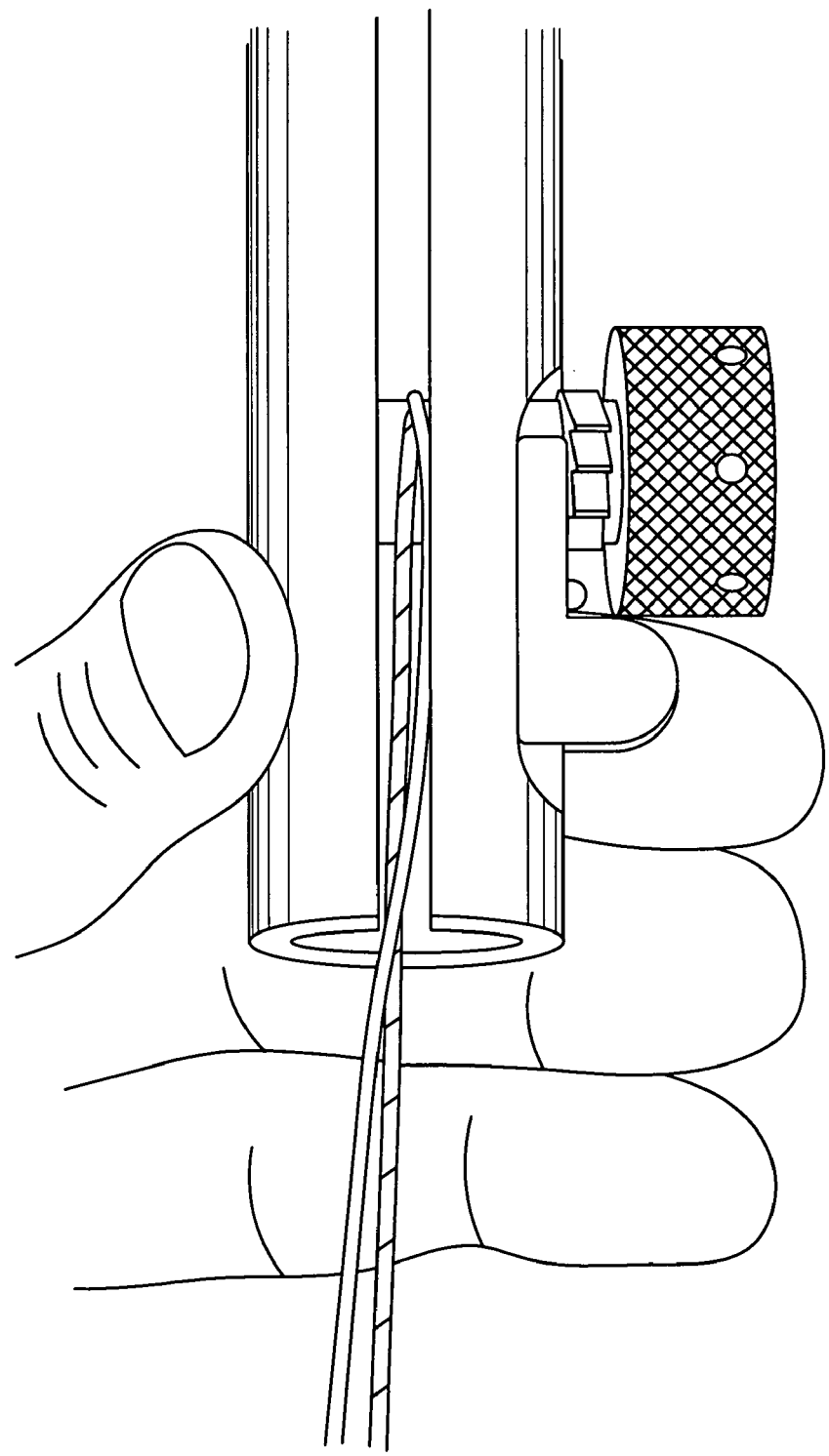
Figure 10C:
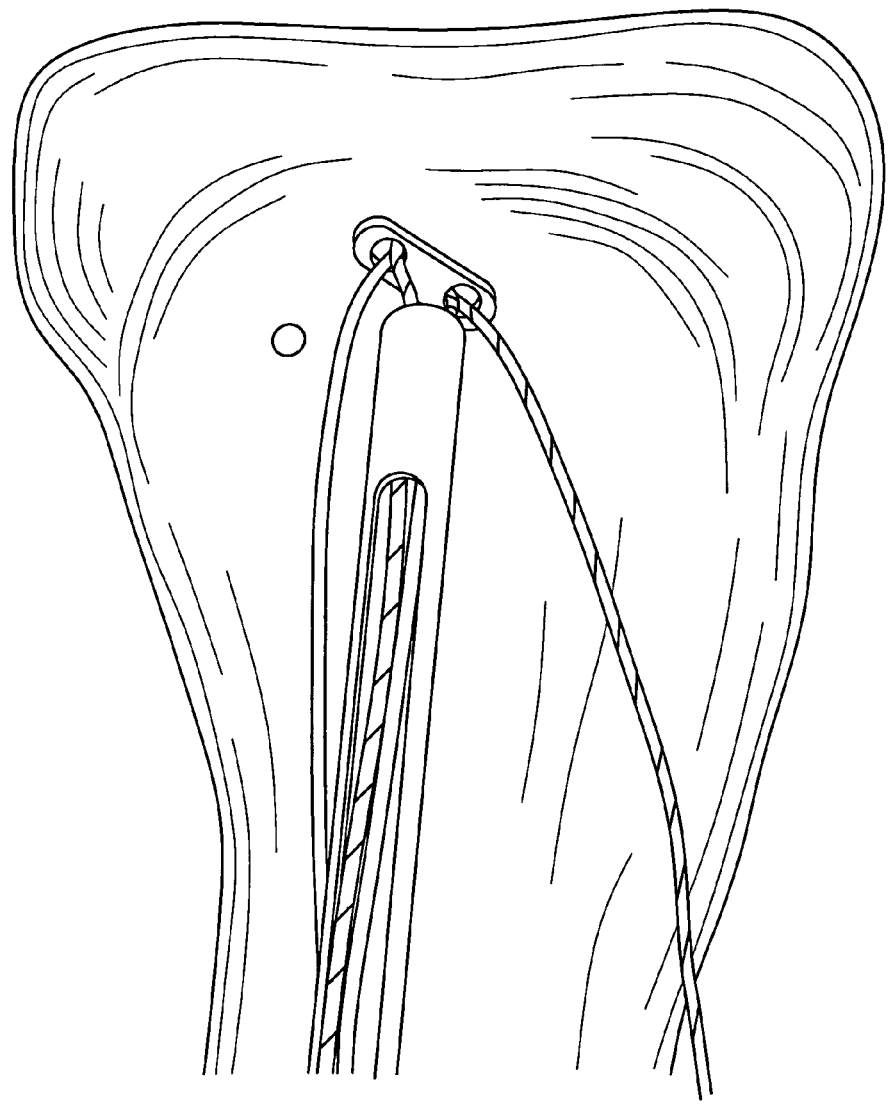
Figure 11A:
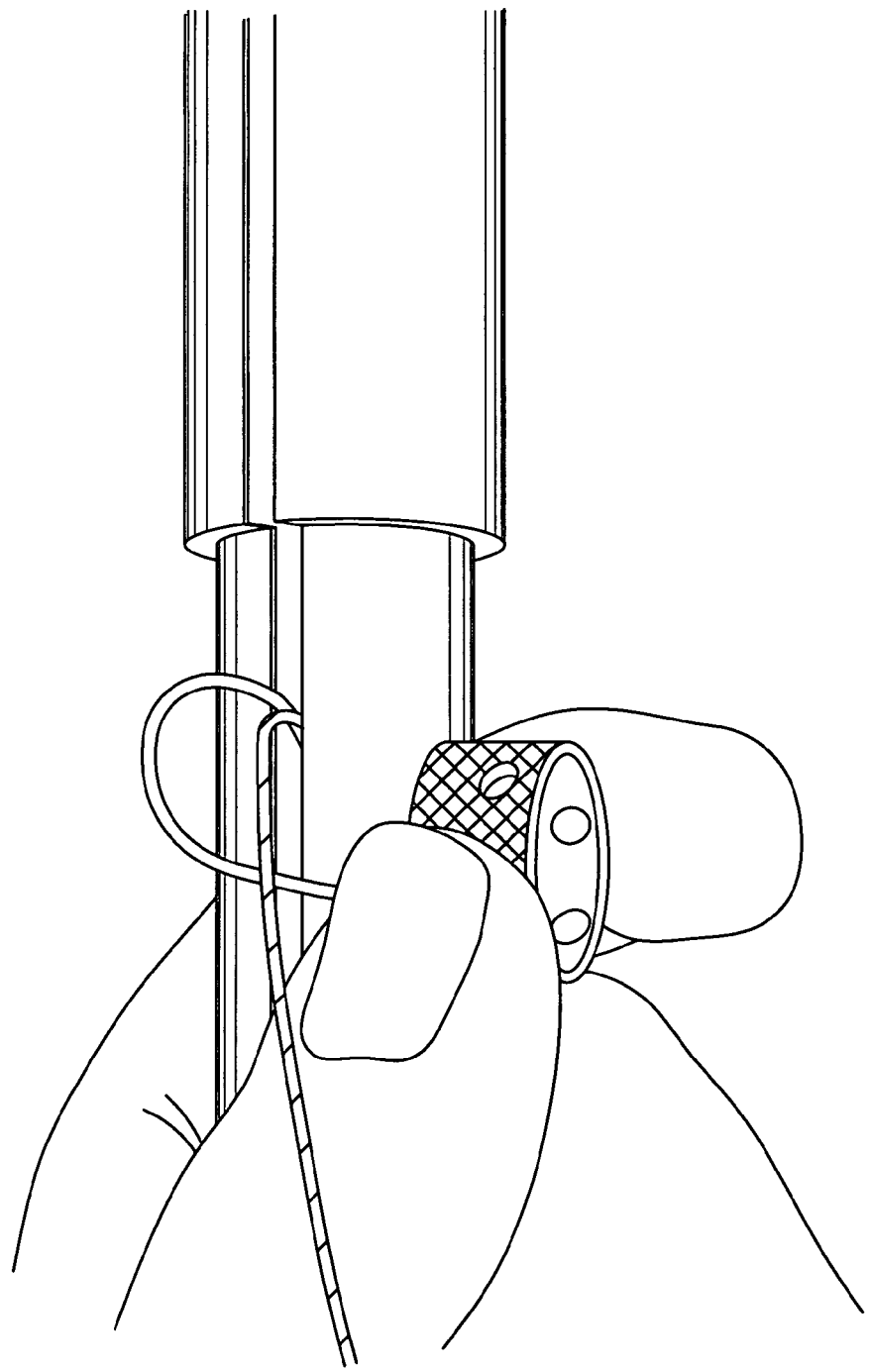
Figure 11B:
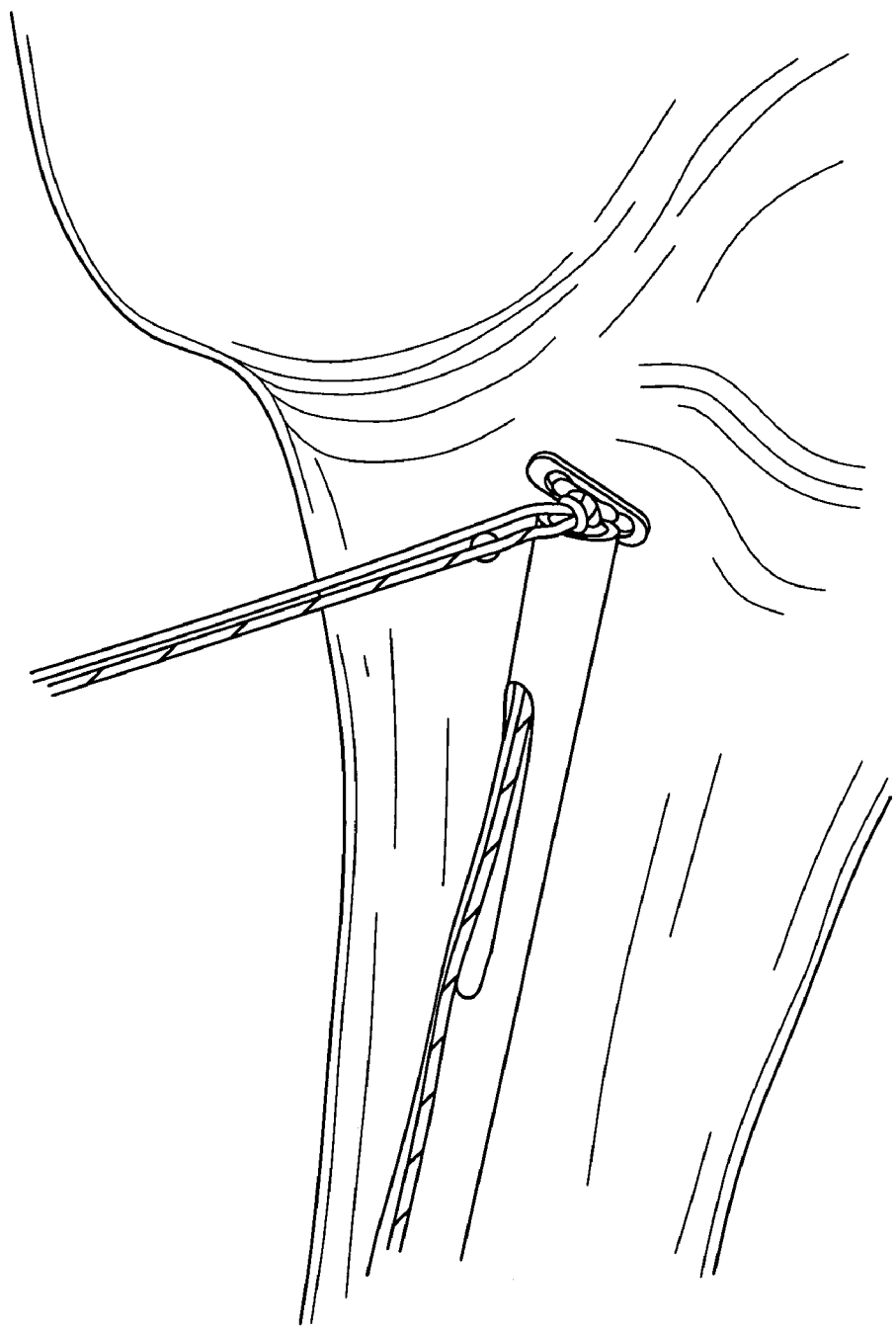
Figure 12A:
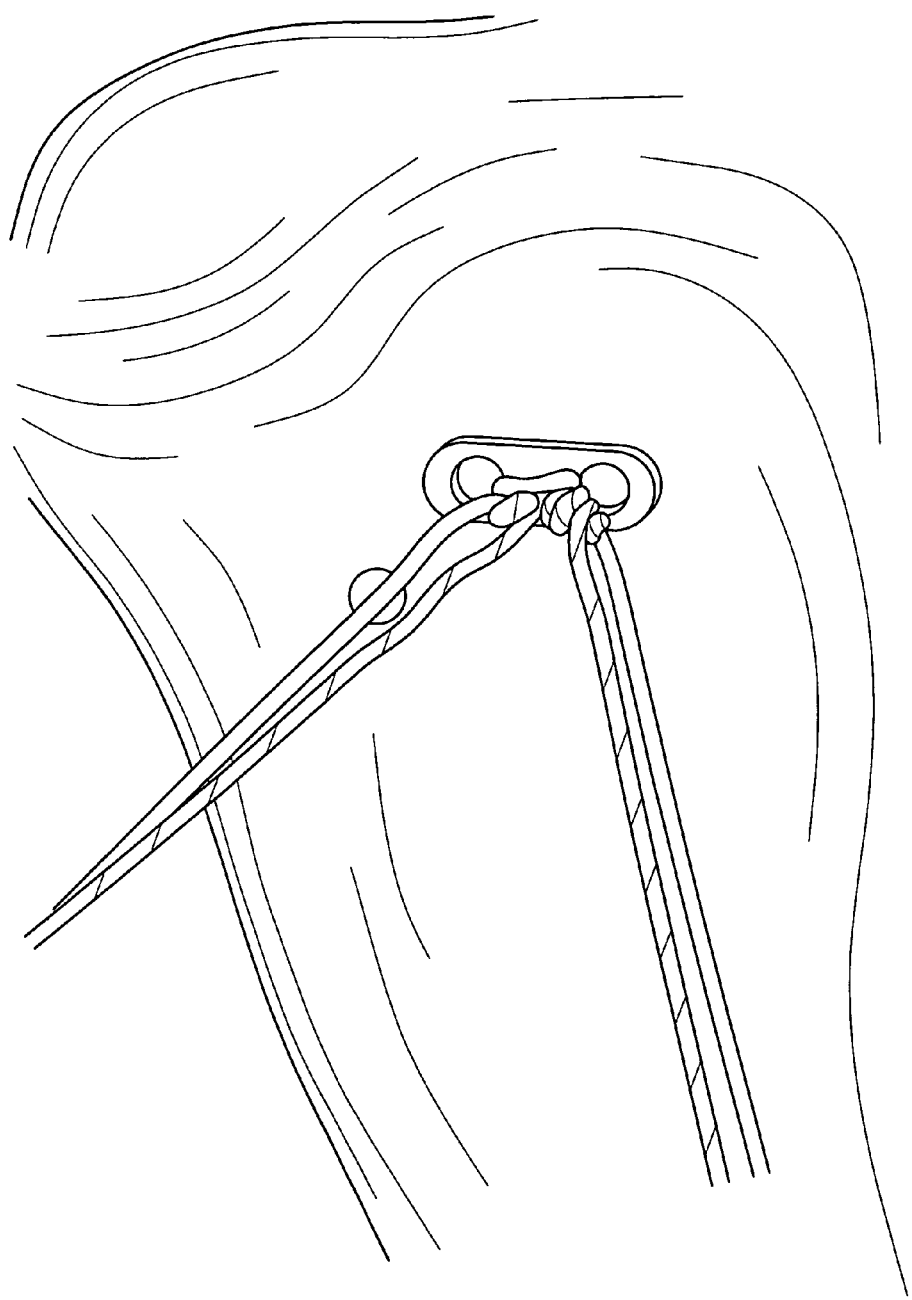
Figure 12B:
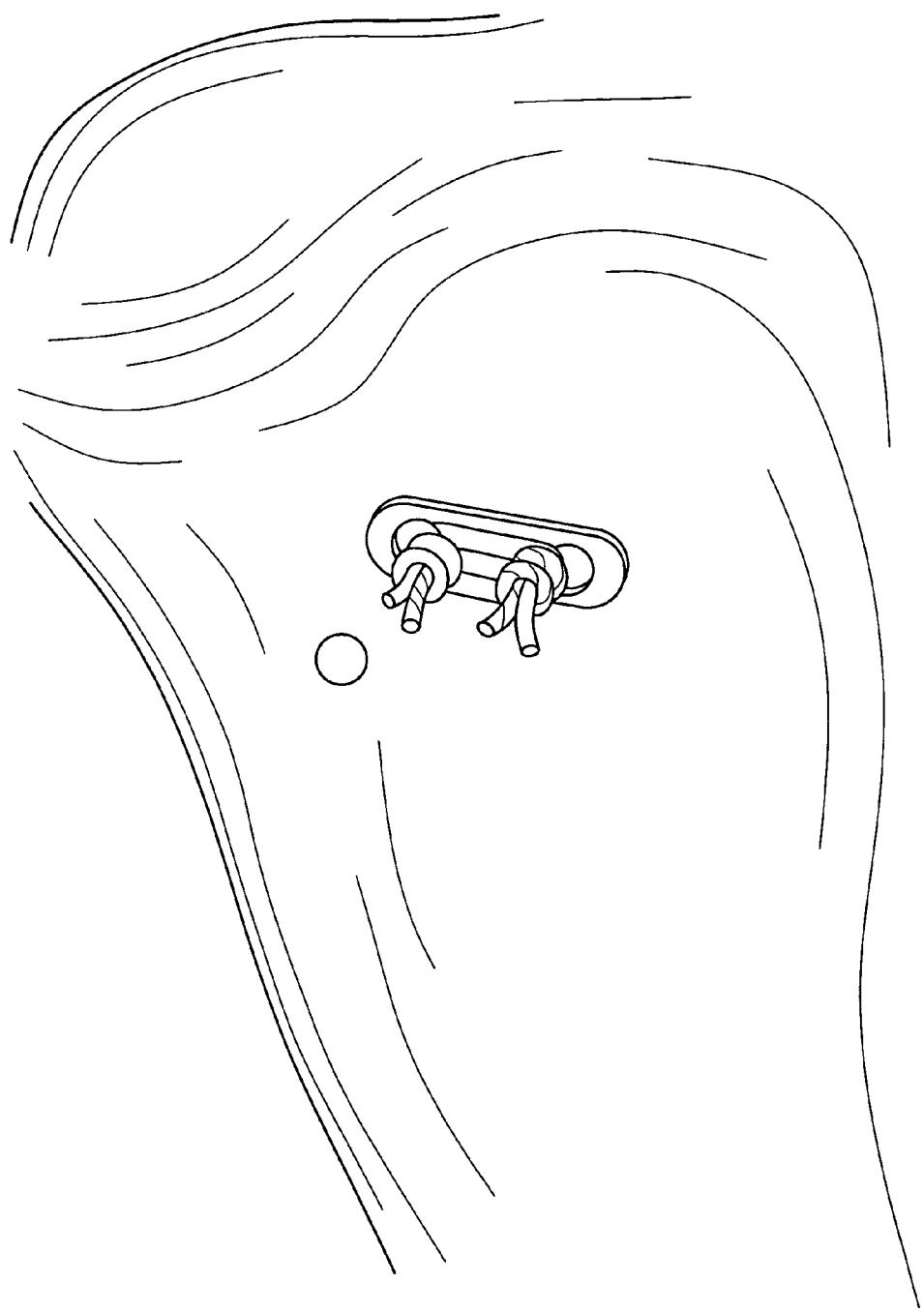

One suture from each graft is then passed through suture tensioner device 300 as shown in FIG. 10(a)-10(c). As shown in FIG. 11(a), the sutures are tensioned to the desired tension (as read on the handle of device 300). The two free sutures are tied together (FIG. 11(b)). Suture tensioner 300 is released and the remaining sutures are tied together (FIGS. 12(a) and 12(b)).

Figure 14A:
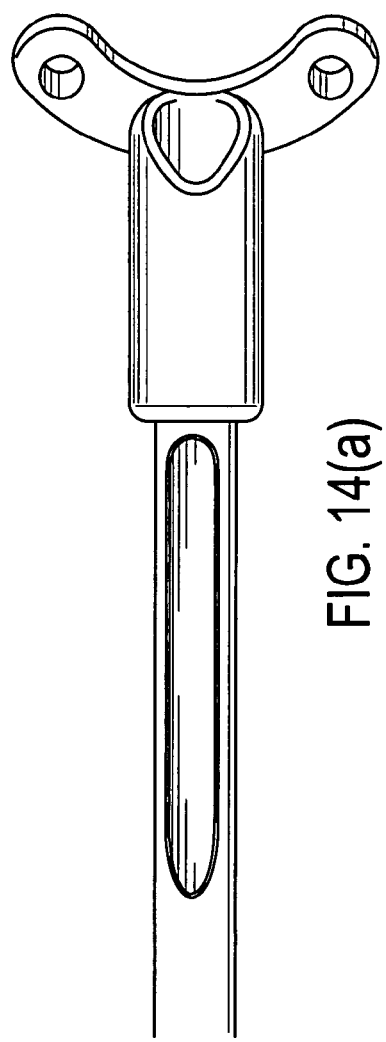
FIGS. 14(a), 14(b), 15(a) and 15(b) illustrate a modular foot piece that may be employed with the suture tensioning device of FIG. 13.
Figure 14B:
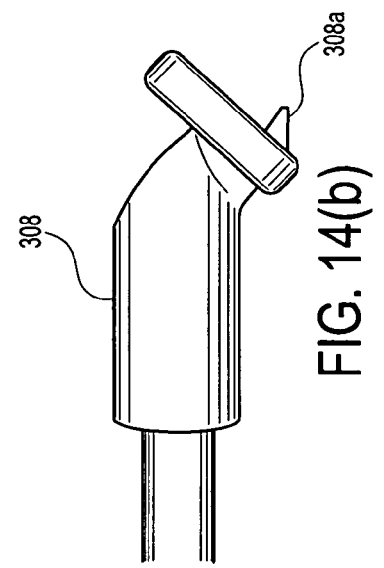
Figure 15A:
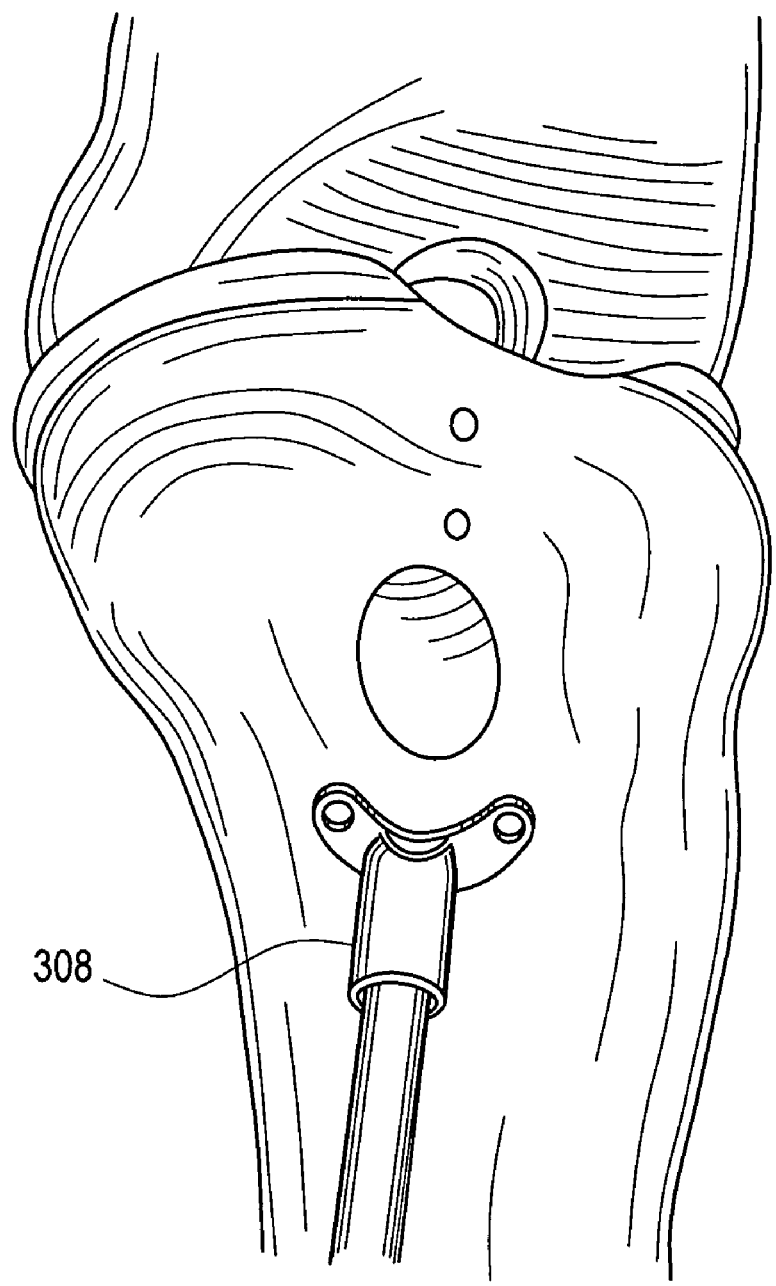
Figure 15B:
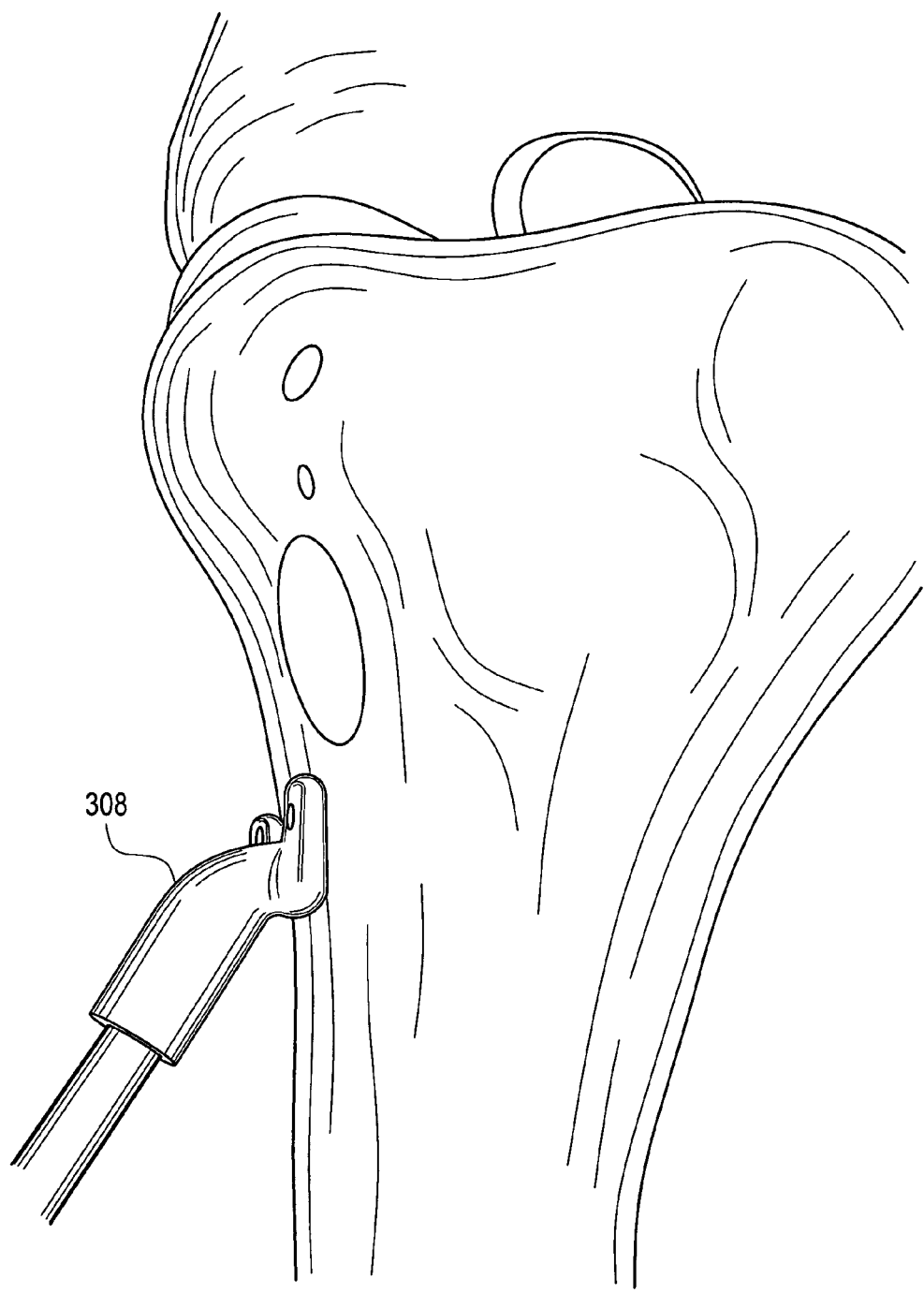

FIG. 13 illustrates suture tensioner 300 (with calibrated spring handle) of the present invention with suture threaded therein. FIGS. 14(a), 14(b), 15(a) and 15(b) illustrate the suture tensioner 300 (with calibrated spring handle) of the present invention with suture threaded therein and also with a stabilizing device which is a modular foot piece 308 (similar to the foot piece 3 illustrated above) which may be used with full tibial tunnels. As shown in FIG. 14(b), for example, stabilizing device (modular foot piece) 308 is provided with three spikes 308a, to self stabilize on tibial cortex. FIGS. 15(a) and 15(b) depict the placement of foot piece 308 on the tibia, adjacent to a full tibial tunnel (or socket).

Suture tensioning device 100, 200, 300 described above may be also employed in additional surgical applications that require suture tensioning, for example, in shoulder applications where the device may be employed as both a knot pusher and a suture tensioner.

For the purposes of the present invention, the term "high strength suture" is defined as any elongated flexible member, the choice of material and size being dependent upon the particular application. For the purposes of illustration and without limitation, the term "suture" as used herein may be a cable, filament, thread, wire, or any other flexible member suitable for tissue fixation in the body. In a preferred embodiment of the invention, the suture comprises a high strength suture sold by Arthrex, Inc. under the tradename FiberWire®.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of tensioning a strand of suture, comprising the steps of:
   looping a strand of suture around a first section of a tissue and a second section of tissue to be joined;
   providing a cannulated suture tensioner comprising:
      a cannulated tube having a proximal end and a distal end;
      a handle attached to the proximal end of the cannulated tube, the handle being configured to allow a strand of suture to pass through at least a portion of the cannulated tube and through the handle; and
      an adjustment device located on the handle, the adjustment device being adapted to be coupled to an end of the strand of suture passing through the cannulated tube and the handle, such that rotation of the adjustment device adjusts suture tension, the adjustment device being provided with a structure for capturing the strand of suture; and
      two springs compressibly disposed between the cannulated tube and the handle for biasing the tube and the handle apart;
   removing the adjustment device from the handle;
   advancing a first end of the suture comprising a post leg of a slip knot formed in the suture through the cannulated suture tensioner;
   reinserting the adjustment device over the first end of the suture passing through the cannulated suture tensioner, and securing the end of the suture to the structure of the adjustment device; and
   rotating the adjustment device with the secured end of the suture to adjust the overall length of the suture tensioner and exert tension on the post leg of the slip knot formed in the suture, thereby tightening the loop of suture around the first and second sections of tissue.

2. The method of tensioning a strand of suture according to claim 1, wherein the adjustment device is an adjustment wheel or a knob.

3. The method of tensioning a strand of suture according to claim 1, further comprising the step of securing the end of the suture to at least one cleat of the structure of the adjustment device.

4. The method of tensioning a strand of suture according to claim 1, further comprising the step of determining the amount of tension exerted on the suture by reading a scale provided on the cannulated tube or on the handle of the suture tensioner.

5. The method of tensioning a strand of suture according to claim 1, wherein the first section of a tissue and the second section of a tissue include bone.

6. The method of tensioning a strand of suture according to claim 1, wherein the first section of a tissue includes bone and the second section of a tissue includes soft tissue.

7. The method of claim 1, wherein the suture comprises wire.

8. The method of claim 1, wherein the suture is formed of a bioabsorbable material.

* * * * *